US00PP25980P3

(12) United States Plant Patent
Zary

(10) Patent No.: US PP25,980 P3
(45) Date of Patent: Oct. 13, 2015

(54) HYBRID TEA ROSE PLANT NAMED 'JACELSPE'

(50) Latin Name: *Rosa hybrida*
Varietal Denomination: JACelspe

(71) Applicant: J & P Park Acquisitions, Inc., Columbia, SC (US)

(72) Inventor: Keith Zary, Troy, OH (US)

(73) Assignee: J & P Park Acquisitions Inc., Columbia, SC (US)

( * ) Notice: Subject to any disclaimer, the term of this patent is extended or adjusted under 35 U.S.C. 154(b) by 107 days.

(21) Appl. No.: 13/998,637

(22) Filed: Nov. 19, 2013

(65) Prior Publication Data

US 2015/0143591 P1 May 21, 2015

(51) Int. Cl.
*A01H 5/02* (2006.01)

(52) U.S. Cl.
USPC ..... Plt./136

(58) Field of Classification Search
USPC ..... Plt./101, 130, 136
See application file for complete search history.

(56) References Cited

U.S. PATENT DOCUMENTS

PP5,165 P 12/1983 Kriloff
PP11,482 P 8/2000 Zary

*Primary Examiner* — Susan McCormick Ewoldt
(74) *Attorney, Agent, or Firm* — McKee, Voorhees & Sease, PLC

(57) ABSTRACT

A new variety of Hybrid Tea rose suitable for garden decoration, having flowers coral pink to coral coloration.

1 Drawing Sheet

Classification: The present invention relates to a new *Rosa hybrida* plant.

Variety denomination: The new plant has the varietal denomination 'JACelspe'.

BACKGROUND OF THE INVENTION

This invention relates to a new and distinct variety of Hybrid Tea Rose. It has as its seed parent the variety known as 'JACshaq' (U.S. Plant Pat. No. 11,482) and as the pollen parent 'JACpribe' (U.S. Plant Pat. No. 18,553).

SUMMARY OF THE INVENTION

Among the features which distinguish the new variety from other presently available and commercial rose cultivars known to the inventor are the following combinations of characteristics, an attractive coral colored flower that intensifies with age, strong upright and vigorous growth habit, long straight stems for cutting, long vase life and an excellent high-centered flower form. The plant has a bushy upright growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'JACelspe' may be asexually propagated by cuttings, budding and grafting. The budding and grafting successfully occurred on the plant/rootstock *Rosa hybrida* cv. Dr. Huey (not patented). The most vigorous plants are produced by budding.

COMPARISON WITH PARENTS

The new rose may be distinguished from its seed parent, 'JACshaq' by the following combination of characteristics:

whereas 'JACshaq' bears flowers that are a creamy white with a pink blush on the petal edges, 'JACelspe' has flowers that are coral in color. 'JACshaq' is also a taller hybrid tea ranging from 150 to 180 cm in height while 'JACelspe' is 120 to 150 cm in height.

The new variety may be distinguished from its pollen parent, 'JACpribe' by being lighter in color (less red), and by having more petals than 'JACpribe'. The new variety is classified as a Hybrid Tea rose with a bushy upright growing habit.

COMPARISON WITH THE CLOSEST COMMERCIALLY AVAILABLE CULTIVAR

The new variety may be distinguished from its closest commercially available cultivar, 'KRIcarlo' (U.S. Plant Pat. No. 5,165) by the following combination of characteristics: whereas 'KRIcarlo' bears double flowers with 30 petals, 'JACelspe' bears double flowers with 40-45 petals. The new variety has a bushy upright growing habit (about 130 to 150 cm in height), whereas the closest commercially available cultivar has a bushy upright habit and is significantly taller (about 150 to 180 cm in height).

BREIF DESCRIPTION OF ILLUSTRATION

The accompanying photograph illustrates the new variety and shows the flowering thereof from bud to full bloom depicted in color as nearly correct as it is possible to make in a color illustration of the character.

The branches used for the photograph came from 3 to 4 year-old rose plants of the new variety grown outdoors in Tipp City, Ohio in the month of July. Throughout this specification, color references and/or values are based upon The Colour Chart of The Royal Horticultural Society (2001) except where common terms of color definition are employed.

DESCRIPTION OF THE NEW VARIETY

The following description is of 3 to 4 year-old rose plants of the new variety grown outdoors in Tipp City, Ohio in the month of July. Phenotypic expression may vary with environmental, cultural and climatic conditions, as well as differences in conditions of light and soil.

FLOWER

The new variety bears medium to large-sized blooms borne singly or is very small clusters of three flowers. Flowers are borne on strong, medium length stems 50 to 70 cm in length and 10 mm in diameter. Outdoors, the plant blooms abundantly and nearly continuously during the growing season. The flowers have only a very slight fruity fragrance.

BUD

The bud is about 3.5 to 4.0 cm long and about 3.0 to 3.5 cm in diameter when the petals start to unfurl. The bud is long and pointed ovoid in shape. As the petals open (after the calyx breaks), the bud is about 4.5 to 5.0 cm in diameter at the widest point, about 4.0 to 4.5 cm in length, and moderately globose in form. When the sepals first divide, the bud color is 37B. When half blown, the upper sides of the petals are 38B in color and the lower sides of the petals are 38B.

The sepals are about 25 mm in length and about 11 mm in width at the widest point. The color of the sepal is 138B on the upper surface and 146B on the lower surface. The outer surface of the sepal is smooth and bears about 2 foliaceous appendages. The inner surface of the sepal is covered with fine wooly tomentum; sepal margins are lined with many glands and hairs.

The peduncle is stiff and erect, medium in length (about 6.0-8.0 cm), and of average caliper (about 5 mm in diameter). It is rough, prickly and glandular. Peduncle color is 146D sometimes with an overlay of 178B.

The receptacle of the flower is funnel shaped and medium in size (about 12 mm in length and about 10 mm in diameter). Its surface is smooth with only an occasional gland. The receptacle color is 146C.

BLOOM

When fully open, the bloom ranges from about 10-12 cm diameter with the largest flowers expressed under cool night time temperatures. Petalage is double with about 40-45 petals under normal conditions. When first open, the bloom form is very high centered and the petals are imbricated with petal edges somewhat reflexed outward. The bloom flattens out somewhat over time as the flowers opens.

PETALS

The substance of the petals is thick and leathery with a smooth surface. The petals are about 5.0 to 5.5 cm in length and about 4.5 to 5.0 cm in width at the widest point. The shape of the petals is orbiculate and flat with rounded apices. Petal margins are entire. Petals are arranged in an imbricated fashion and drop off of the plant cleanly before dying. Petals last on the plant for about 7 days. As a cut flower the petals last about 10 days.

Petaloids number from 2 to 11 and are 38B in color. Petaloids are about 1.5 cm to 3.5 cm in length and about 1.5 to about 2.5 cm in width at the widest point. Petaloids are irregularly shaped somewhat obovate to oblanceolate with rounded apices.

NEWLY OPENED FLOWER

The upper side of the petals is 38B in color on the newly opened flower. The reverse side of the petals is 38B in color. The base of the petals has a large color spot of about 0.7 cm to 0.8 cm by about 1.5 cm with a color of 5A. The under and upper surface colors of the petaloids are similar in coloration to the upper and under surfaces of the petals.

The general tonality at the end of the first day is no change.

THREE-DAY-OLD FLOWER

At the end of the third day the tonality is generally unchanged. By day 5 the color of the petals intensifies to 39B and the petal spot fades to 1C. The under and upper surface colors of the petaloids are similar in coloration to the upper and under surfaces of the petals.

MALE REPRODUCTIVE ORGANS

Stamens average about 80 to 90 in number and are about 7.0 to 8.0 mm in length. Anthers are 0.3 cm in length with color of 19A. Anthers are arranged regularly around the styles and mixed with petaloids.

Filaments are of average length (about 3 to 4 mm) and are 158C in color. Pollen is sparse and is 22A in color.

FEMALE REPRODUCTIVE ORGANS

Pistils vary in number (average about 50). Styles are moderately even, average in length (about 4 mm), moderately heavy in caliper, and bunched. Style color is 184C.

Stigmas are 156D in color and 1.0 mm in length. Ovaries are usually all enclosed in the calyx.

Hips have not been observed on this variety when grown in Tipp City, Ohio.

FOLIAGE

The compound leaves are usually comprised of three to seven leaflets and are borne abundantly. The five-leaflet leaves are about 12 cm long and 9 cm wide.

The terminal leaflets are pointed oval in shape. The base is rounded oblique in shape and the apex shape is acuminate. The upper side of the leaves is leathery and glossy with a single serrated edge. The terminal leaflets are about 5.2 to about 5.6 cm in length and about 3.1 to about 3.4 cm in width at the widest point New foliage is 178C in color on the upper side and 178A in color on the lower side. Old foliage is 139A on the upper side and 137C on the lower side.

The vein color of the leaves is 147B and the venation pattern is reticulate.

The rachis is average in caliper and rough. The upper side is shallowly grooved with many hairs and few stipitate glands on the edges of the grooves. The underside of the rachis is rough with some hairs and few small prickles. The rachis color is 138B.

The stipules are about 8 to 12 mm in length and about 4 mm in width. They have serrated edges. The auricle is subulate in shape. The stipules color is 138B and can be partially overlain with 182B.

The petiole is average in caliper and rough. The upper side is shallowly grooved with many hairs and few stipitate glands on the edges of the grooves. The underside of the petiole is rough with some hairs and few small prickles. The petiole is about 7.0 to about 9 mm in length and about 0.1 to about 0.2 cm in width at the widest point. The petiole color is 138B.

The plant displays an above average degree of resistance to rust and powdery mildew and is susceptible to black spot as compared to other commercial varieties grown under comparable conditions in Tipp City, Ohio. 'JACelspe' is cold hardy without protection through zone 6 and is winter hardy in zone 5 with protection.

GROWTH

The plant has a bushy upright growing habit (about 120 to 130 cm in height and about 100 to 120 cm spread at the widest point), with full branching. It displays very vigorous growth and the canes are strong (about 1.5 to about 2.2 cm in diameter at the widest point).

Stems of new wood are 147B in color. Stems of old wood are 137B in color. The new wood and the old wood bear some large prickles. The prickles are moderately hooked downward with a short narrow oval base. Prickles are of 8 to 10 mm in length. Young prickles are 173C in color. When mature, prickles are 200C in color.

There are no small prickles on the main stalk or lateral stalks.

I claim:

1. A new and distinct Hybrid Tea rose plant of the variety substantially as described and illustrated herein.

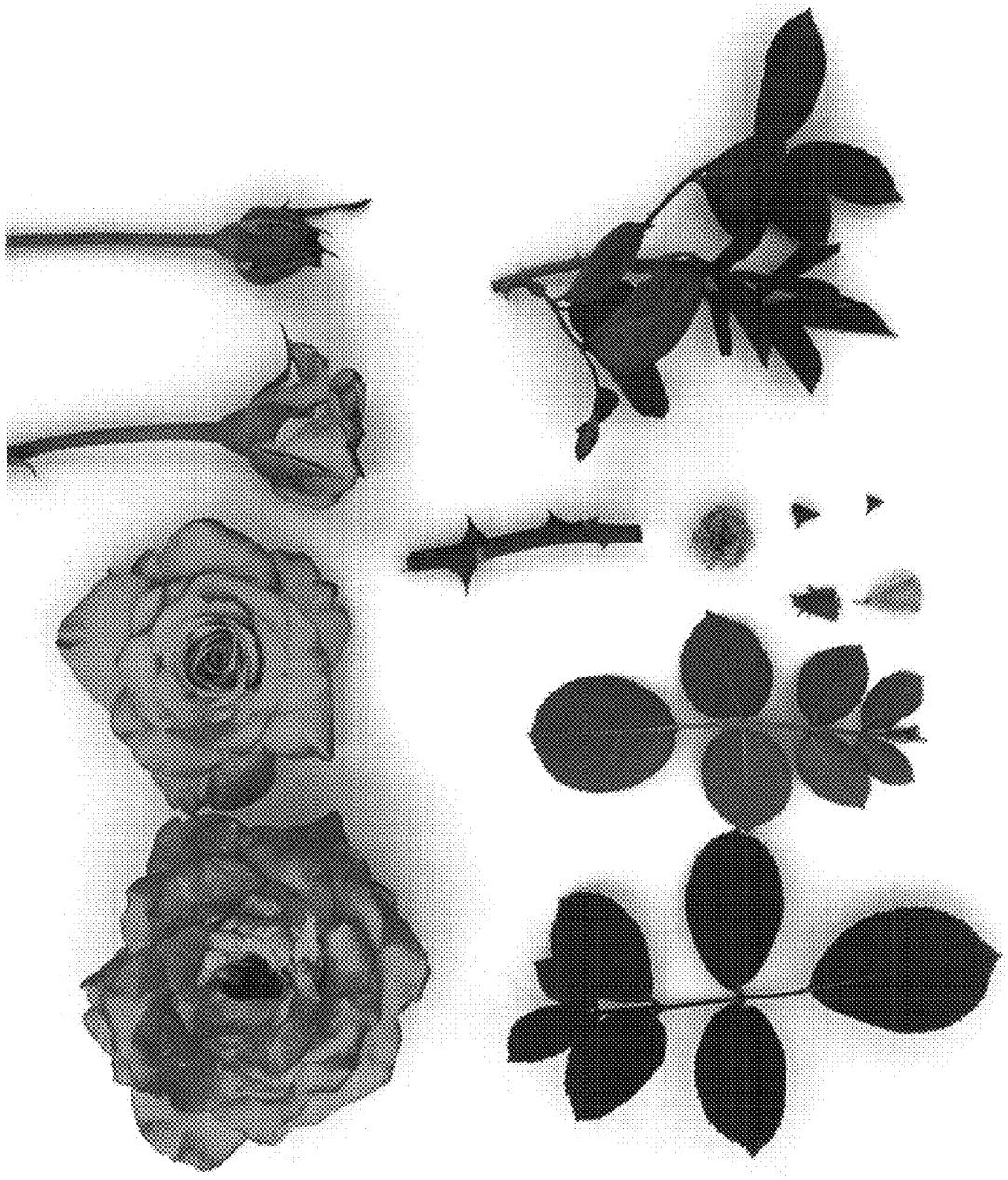

* * * * *